United States Patent [19]

Gray et al.

[11] 4,271,033

[45] Jun. 2, 1981

[54] TRANSITION METAL COMPLEX CATALYSTS

[75] Inventors: Harry B. Gray, Pasadena, Calif.; Kent R. Mann, Roseville, Minn.

[73] Assignee: California Institute of Technology, Pasadena, Calif.

[21] Appl. No.: 68,100

[22] Filed: Aug. 20, 1979

[51] Int. Cl.³ .................... C07D 301/04; B07D 301/22
[52] U.S. Cl. .................. 252/188.3 R; 137/3; 252/186; 260/348.32; 260/348.33; 260/687 R
[58] Field of Search ............. 252/188.3 R, 372, 186; 137/3; 260/348.32, 687 R, 687 H, 348.33

[56] References Cited

U.S. PATENT DOCUMENTS

| | | | |
|---|---|---|---|
| 3,210,380 | 10/1965 | Sharp et al. | 260/348.32 |
| 3,259,638 | 7/1966 | Allison | 260/348.32 |
| 3,702,619 | 11/1972 | Son | 137/88 |
| 3,706,534 | 12/1972 | Verheul et al. | 260/348.34 |
| 3,989,526 | 11/1976 | Bissonette | 252/188.3 R |

Primary Examiner—Deborah L. Kyle
Assistant Examiner—Irwin Gluck
Attorney, Agent, or Firm—Poms, Smith, Lande & Rose

[57] ABSTRACT

Substrates are oxidized by means of two-oxidative addition reactions of a dimeric, dinuclear transition metal complex oxidant containing four binucleating diisocyanide bridge ligands. The complex is reoxidized by means of a secondary oxidant which is a stronger oxidizing agent than the complex which in turn is oxidized by molecular oxygen. Though the direct oxidation of the complex by oxygen involves a large energy barrier and is relatively slow, the kinetics of the two stage oxidation of the complex by the secondary oxidant and of the oxidant by oxygen permit regeneration of the oxidant at reasonable rate. Substrates, such as the olefins, ethylene or propylene, have been continuously oxidized by bubbling oxygen and the olefin through a solution of a dimeric, dirhodium complex containing four 1,3-diisocyanopropane bridge ligands and a secondary oxidant such as a cerium salt.

19 Claims, 2 Drawing Figures

TRANSITION METAL COMPLEX CATALYSTS

ORIGIN OF THE INVENTION

The Government has rights in this invention pursuant to Grant No. CHE77-11389 awarded by the National Science Foundation.

BACKGROUND OF THE INVENTION

1. Field of the Invention

The present invention relates to metal-organic complex oxidation catalysts and, more particularly, to a combination of a dinuclear transition metal-tetra-diisocyanide complex with a stonger oxidant.

2. Description of the Prior Art

Dinuclear transition metals complexed with four binucleating diisocyanides bridge ligands have previously been reported. The dirhodium tetra-diisocyanopropane dimers undergo two-center oxidative addition reactions with several substrates. The orbital interactions between the directly coupled metal centers give rise to striking electronic absorption properties, the most prominent being a low-lying system attributable to the $^1A_{1g} \rightarrow {}^1A_{2u}(1a_{2u} \rightarrow 2a_{1g})$ excitation.

The dimeric complex are very interesting oxidizing agents in multielectron redox processes since each metal center can furnish or remove one or more electrons from a substrate. Though analogous monomeric metal complexes are not good oxidation catalysts, the dimers have shown good oxidation properties with numerous substrates, probably due to the capability of the binucleating ligands to maintain or reduce metal-metal spacing on oxidation. However, the redox reactions are stoichiometric requiring reoxidation of the complex. The complex has been shown to be readily oxidized by halogens such as bromine, chlorine or iodine. Oxidation by molecular oxygen or air would be desirable for industrial processes due to formation of a peroxide intermediate at low cost. However, the direct oxidation by oxygen is relatively slow due to the large energy barrier for this reaction. Peroxidic intermediates are also of value due to the selectivity in certain reactions such as in the oxidation of olefins such as propylene to propylene oxide under mild conditions while minimizing formation of by-products.

Present commercial processes for producing propylene oxide suffer from one or more major drawbacks. The chlorohydrin process produces chlorine compounds that pose pollution problems. The oxirane process produces about twice as much styrene or t-butanol co-product as propylene oxide. Other processes under consideration such as peracid or hydrogen peroxide also produce co-product and/or require hydrogen peroxide, an expensive reagent.

SUMMARY OF THE INVENTION

Substrates are oxidized at effective rate in accordance with the invention by oxygenation of a dimeric dinuclear metal complex containing four binucleating biisocyanides in the presence of a secondary oxidant which is a stronger oxidizing agent than the complex. Though the direct oxidation of the complex by oxygen involves a large energy barrier and is relatively slow, the kinetics of the two stage oxidation of the complex by the secondary oxidant and of the oxidant by oxygen permit regeneration of the oxidant at reasonable rate. Substrates, such as the olefins, ethylene or propylene, have been oxidized by bubbling the olefin through a solution of a dimeric, dirhodium complex containing four 1,3-diisocyanopropane bridge ligands and a secondary oxidant such as a cerium salt.

These and many other attendant advantages of the invention will become readily apparent as the invention becomes better understood by reference to the following detailed description when considered in conjunction with the accompanying drawings.

DESCRIPTION OF THE PREFERRED EMBODIMENTS

Figure 1:
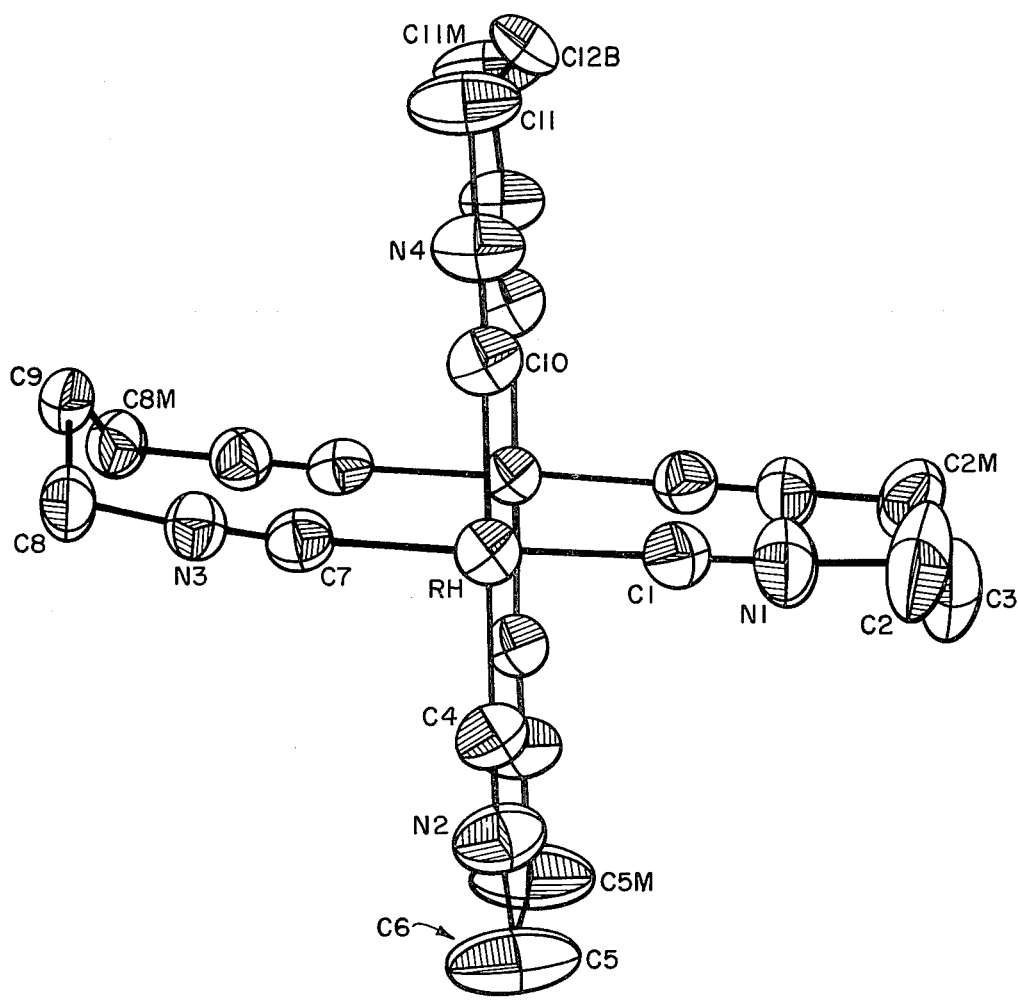
FIG. 1 is a structural formula of reduced rhodium bridge complex.

Substrates are oxidized according to the following general reactions:

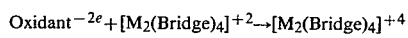

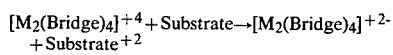

where M is a transition metal and Bridge is a binucleating biisocyanide.

The transition metal can be selected from metals in The platinum group such as rhodium, cobalt, iridium, platinum, palladium, nickel, osmium, ruthenium or iron. The anion is selectively depending on whether the complex is to be utilized in aqueous or organic media. Suitable anions are halides, boron tetrafluoride, tetraphenyl borate or $PF_6^{--}$.

The Bridge ligand can be any binucleating biisocyanide particularly aliphatic biisocyanides containing 2 to 20 carbon atoms such as 1,3-diisocyanopropane, 1,4-diisocyanobutane (4-Bridge), 2,5-dimethyl-2,5-diisocyanohexane (TM-4 Bridge) and cis-1-isocyano-4(2-isocyanopropyl)cyclohexane (Cyclo-5-Bridge).

The structure and names of other binucleating biisocyanides are illustrated in Tables 1 and 2 which follow:

TABLE 1

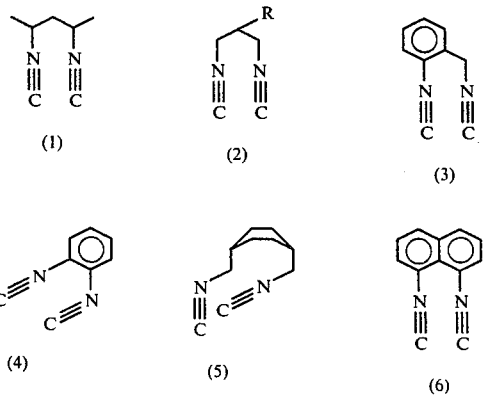

TABLE 1-continued

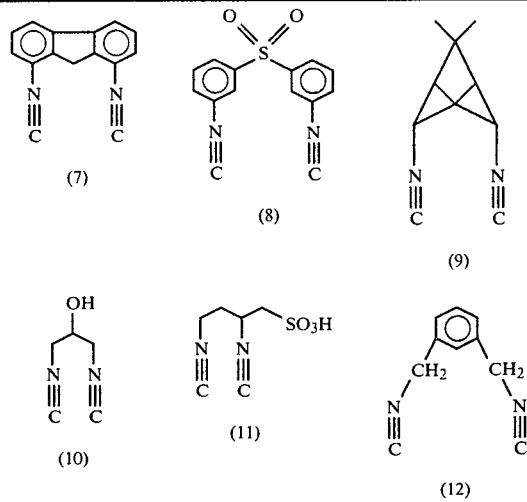

TABLE 2
NAMES OF LIGANDS 1. 2,4 diisocyano pentane
2. 2-substituted-1,3-diisocyanopropane
3. 1-isocyano benzylisocyanide
4. 1,2-diisocyanobenzene
5. 1,4-diisocyanocyclohexane
6. 1,8-diisocyanonaphthalene
7. 1,8-diisocyanofluorene
8. m-diisocyanophenyl sulfone
9. 1,3-diisocyano 2,2,4,4 tetramethylcycolbutane
10. 1,3-diisocyano diisocyano 2 hydroxy propane
11. 3,5-diisocyano butanesulfonic acid
12. α, α' diisocyano-oxylene Salts of the reduced complexes are prepared by addition of the biisocyanide bridge ligand to a stoichiometric amount of [Rh(COD)Cl]$_2$ in solvent where COD is cyclooctadiene. The latter compound was synthesized by a standard method: J. Chatt and L. M. Venanzi, J. Chem. Soc., 4735 (1957). Experiments follow:

EXAMPLE 1

1,3-diisocyanopropane(bridge)

To a 3 liter, 3-necked flask equipped with overhead stirrer and two Claisen condensors was added 600 ml of a 50% aqueous solution of NaOH (prepared by mixing excess solid NaOH and water and allowing the phases to come to equilibrium at 25° C. over several days) and 170 ml (2.1 moles) of chloroform. 500 ml of dichloromethane was added as solvent, followed by 84 ml (1 mole) of 1-3-diaminopropane (Aldrich Chemical Company) and finally, 2.1 g of the phase-transfer catalyst, benzyl-triethylammonium chloride. The mixture was then rapidly stirred until refluxing of the dichloromethane was observed. When the rate of reflux becomes excessive, the stirring rate is decreased to slow the reaction; caution is advised, as pressure explosions of solvent gushing out the condensors may occur if the reaction rate is too rapid. The flask temperature should be maintained at about 40° C. for 30 minutes, after which the stirring may be accelerated once again. The reaction mixture is stirred for about three additional hours, and the solution will have darkened slightly due to formation of polymeric side product. The layers are separated, and the organic phase is washed four times with 500 ml portions of water. The solvent is then removed, and the ligand is purified by vacuum distillation. The bridge distills at 55° C. at 1 mm Hg as a clear liquid. Use extreme care while distilling the product. The infrared spectrum of the ligand shows a very strong and narrow $\nu$ (C≡N) stretch at 2149 cm$^{-1}$, with other prominent peaks at 2930 (m), 1660 (m), and 1490 (s) cm$^{-1}$. The 60 MHz PMR spectrum of bridge exhibits two multiplets integrated in the ratio of 2:1, the first is a triplet of triplets at 3.48 δ (terminal CH$_2$), and the second is a complex multiplet centered at 1.76 δ (central CH$_2$). With small amounts of the material, an alternative, safer purification is elution of crude product with toluene over alumina, with pure bridge being the first fraction off the column.

EXAMPLE 2

Rh$_2$(L)$_4$PF$_6^-$, L=TM 4-Bridge or Cyclo 5-Bridge were prepared as follows: 0.630 g AgPF$_6$ (2.5 mmol) was added to 25 ml of a stirred acetonitrile solution containing 0.616 g (1.25 mmol) [Rh(COD)Cl]$_2$. The AgCl precipitate was filtered and then either 0.822 g of Tm 4-Bridge or 0.95 g Cyclo 5-Bridge was added to the light yellow filtrate. Diethyl ether was added and the resulting precipitate was recrystallized from acetonitrile/ether and air dried.

Yields were about 80%. Rh$_2$ (TM 4-Bridge)$_4$(PF$_6$)$_2$-Anal. Calcd: C, 41.68; H, 5.60; N, 9.72. Found: C, 41.38; H, 5.47; N, 10.08; $\nu$(CN) 2152 cm$^{-1}$ Ch$_2$Cl$_2$. Rh$_2$(Cyclo 5-Bridge)$_4$(PF$_6$)$_2$-Anal. Calcd: C, 45.87; H, 5.77; N, 8.92. Found: C, 46.01; H, 5.60; N, 9.09; $\nu$(CN) 2160 cm$^{-1}$ CH$_2$Cl$_2$ solution.

4-Bridge TM 4-Bridge, and Cyclo 5-Bridge were prepared from the corresponding amine by the method of W. P. Weber, et al., Angew. Chem. Internat. Ed., 11, 530 (1972). 4-Bridge was purified by vacuum distillation; TM 4-Bridge and Cyclo 5-Bridge were purified by recrystallization from CH$_2$Cl$_2$. The infrared spectra and NMR spectra are as follows: bridge'; IR, 2145 cm$^{-1}$ $\bar{\nu}$(CN), neat; TM 4-Bridge, IR, 2126 cm$^{-1}$ $\bar{\nu}$(CN) CH$_2$Cl$_2$; NMR.

EXAMPLE 3

Co$_2$ (TM 4-Bridge)$_4$ (CoCl$_4$)$_2$.4 H$_2$O

To a stirred solution of 0.30 g (1.26 mmoles) of CoCl$_2$.6 H$_2$O in 50 ml of anhydrous ethanol was added 0.25 g (1.52 mmoles) of TM 4-Bridge. The resulting green solution was refrigerated for three days affording green crystal of Co$_2$ (TM 4-Bridge)$_4$(CoCl$_4$)$_2$.4 H$_2$O.

Calcd: C, 38.49; H, 5.30%; N, 8,89%. Found: C, 38.49%; H, 5.813%, 8.98%.

EXAMPLE 4

Rh$_2$ (Bridge)$_4$(BF$_4$)$_2$

To a solution of 1.23 g of (Rh(COD)Cl)$_2$ in 20 ml of acetonitrile was added 0.97 g of silver tetrafluoroborate in 10 ml of acetonitrile. The solution was stirred and filtered by gravity to remove the silver chloride formed. Then 0.94 g of 1,3-diisocyanopropane bridge in 10 ml of acetonitrile was added dropwise with stirring to the rhodium solution. The purple powder was filtered, washed with diethyl ether, and dried in vacuo. This salt is soluble in acetonitrile, DMF, and DMSO.

Calcd: C, 31.78; H, 3.20; N, 14.82; F, 20.11. Found: C, 31.62; H, 3.37; N, 14.66; F, 19.82.

EXAMPLE 5

Rh$_2$(Bridge)$_4$Cl$_2$

This compound was obtained by adding a stoichiometric amount of 1,3-diisocyanopropane bridge to a chloroform solution of (Rh(COD)Cl)$_2$ and filtering the blue precipitate, washing with diethyl ether, and drying in vacuo. Soluble in methanol, water, DMSO and DMF.

EXAMPLE 6

1.1 g 4-bridge was dissolved in 100 ml CHCl$_3$. 10 ml of this solution was added to 50 ml of CH$_3$CN in an erlenmeyer flask. The resulting solution was purged with nitrogen for 5 minutes. Rh$_2$(CO)$_4$Cl$_2$(0.10 g) in 5 ml CHCl$_3$ was then added dropwise to the 4-bridge while maintaining vigorous stirring and a nitrogen blanket. After complete addition, the solution was deep red purple and some precipitation had occurred. Stirring was maintained for 5 minutes more and an equal volume of diethyl ether was added to precipitate all solids. The resulting dull blue gray powder was washed with CHCl$_3$ and ether and dried under a stream of N$_2$. Once dry, the product was worked up in air. The blue gray powder was extracted with methanol several times. To the filtrate was added solid NaBPH$_4$ (excess). A navy blue product precipitated immediately. This was isolated by filtration, washed with water, methanol and ether. The product was air dried. Yields are in general poor (less than 30% based on Rh$_2$(CO)$_4$Cl$_2$) and variable. The complex obtained in this fashion can be purified by reprecipitation from CH$_3$CN/ether mixtures and gives reproducible UV/VIS and IR spectra consistent with Rh$_2$(4-bridge)$_4$ (BPh$_4$)$_2$.

Elemental analysis (RH$_2$(4-bridge)$_4$(BPh$_4$)$_2$. Anal. Calcd: C, 67.73; H, 5.68; N, 8.78; $\nu$(CN)2170 cm$^{-1}$ KBr pellet. Found: 66.75; H, 5.65; N, 8.99.

The bridged dirhodium complex with 1,3-diisocyanopropane of Example 5, Rh$_2$(1,3-diisocyanopropane)$_4^{2+}$ system has been investigated in more detail. This cation is called rhodium bridge because of the nature of its molecular structure. A view of this cation based on X-ray crystal structure analysis is shown in FIG. 1. The binuclear complex has near D$_{4h}$ symmetry, with a Rh-Rh distance of 3.26 Å. The occupied d$_{z^2}$ oribals on each d$^8$ planar Rh(I) center interact, yielding two MO's of symmetries a$_{1g}$ and a$_{2u}$; and the lowest unoccupied monomer orbitals (of a$_{2u}$ symmetry) also interact and split into a$_{1g}$ and a$_{2u}$ levels in the binuclear complex. The orbitals of interest in discussing the low-lying absorption and emission bands, and the photochemistry, are, in order of increasing energy, 1n$_{1g}$<1a$_{2u}$<2a$_{1g}$<2a$_{2u}$. The ground state of Rh$_2$(bridge)$_4^{2+}$ is $^1$A$_{1g}$(1a$_{1g}^2$1a$_{2u}^2$).

The intense absorption band in the spectrum of Rh$_2$(bridge)$_4^{2+}$ at 553 nm ($\epsilon$ 14,500) in acetonitrile solution is attributed to $^1$A$_{1g}$–$^1$A$_{2u}$ (1a$_{2u}$–2a$_{1g}$), which is an allowed transition. The band falls well to the red of the analogous $^1$A$_{1g}$–$^1$A$_{2u}$ (d$_{z^2}$ –a$_{2u}$) transition in a reference monomeric complex (e.g., this band in the spectrum of Rh(CNEt)$_4^+$ peaks at 380 nm), which illustrates the importance of the axial orbital interactions (d$_{z^2}$–d$_{z^2}$ and a$_{2u}$–a$_{2u}$) in the rhodium bridge binuclear case.

The complex-oxidant-oxygen catalyst system can be used to oxidize any substrate wheter inorganic such as water or carbon monoxide or organic such as olefins such as alkylene containing 2 to 20 carbon atoms, acetylene, alcohols, aldehydes, ketones, etc. The secondary oxidant can be any oxidizing agent stronger than the complex such as salts of cerium, molybdenum, iron$^{+3}$ or cupric metals, quinones, permanganates, (IrCl$_6$)$^{-2}$, dichromates, and the like. The secondary oxidants are present in at least stoichiometric-amount to the rhodium metal and preferably in excess. A source of protons such as hydrochloric or sulfonic acid should also be present in the solution.

Gaseous substrates can be bubbled through the solution while liquid substrates can be added incrementally or at the start of the reaction. The reaction can be conducted at temperatures from 0° C. to 150° C. preferably from 60° C. to 100° C. and at pressures from below atmospheric to 20 atmospheres or more preferably from 1 to 5 atmospheres. The complex concentration can be from 10 to 200 ppm generally from 50 to 150 ppm.

Figure 2:
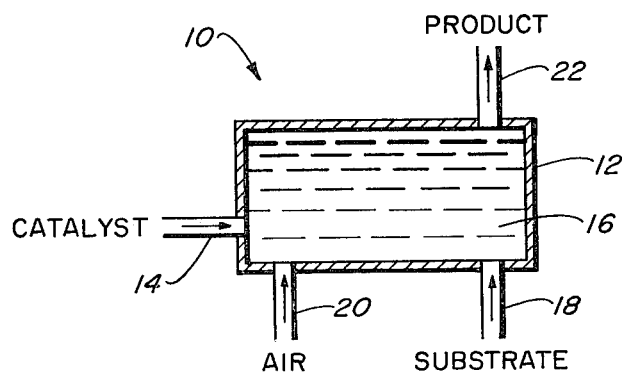
FIG. 2 is a schematic view of a oxidation reactor in accordance with the invention.

Referring now to FIG. 2, the oxidation system 10 includes a reactor 12 having an inlet 14 for feeding in the catalyst solution comprising the metal bridge complex and an excess of secondary oxidant dissolved in solvent such as water. After the solution 16 is charged into the reactor, substrates can be continuously oxidized by bubbling the substrate and air through the solution 16 from inlet 18, 20 respectively. The oxidized substrate is recovered as product through outlet 22.

EXAMPLE 7

The purple BF$_4$ salt (O-IM) of Example 4 was dissolved in methane sulfuric acid. 1 mole of an acidic solution ceric sulfate Ce$^{+4}$ (SO$_4$)$_2$ was added (pH 1). The complex was oxidized to a light yellow form.

EXAMPLE 8

The purple BF$^4$ salt of Example 4 was dissolved in concentrated HCl and air was bubbled through the solution at room temperature. The complex was slowly converted to a yellow oxidized form.

It is to be realized that only preferred embodiments of the invention have been described and that numerous substitutions, modifications and alterations are permissible without departing from the spirit and scope of the invention as defined in the following claims.

What is claimed is:

1. An oxidizing reagent comprising the combination of a dimeric, dinuclear transition metal complex containing four binucleating diisocyanide bridge ligands and a secondary oxidant which is a stronger oxidizing agent than the complex.

2. A reagent according to claim 1 in which the complex and secondary oxidant are dissolved in solution.

3. A reagent according to claim 2 in which the solution contains dissolved molecular oxygen.

4. A reagent according to claim 2 in which the solvent is water.

5. A reagent according to claim 2 in which the solvent is an organic solvent.

6. A reagent according to claim 1 in which the metal is a platinum group metal.

7. A reagent according to claim 6 in which the metal is selected from rhodium, cobalt, iridium, platinum, palladium, nickel, osmium, ruthenium or iron.

8. A reagent according to claim 6 in which the binucleating biisocyanide is selected from compounds of the formula (CN)$_2$R where R is an organic divalent group containing 2 to 20 carbon atoms.

9. A reagent according to claim 8 in which R is selected from alkylene, arylene, alkarylene, cycloalkylene, alkylcyoalkylene or alkarylene.

10. A reagent according to claim 9 in which the biisocyanide is selected from 1,3-diisocyanopropane, 1,4-diisocyanobutane, 2,5-dimethyl-2,5-diisocyanohexane, cis-1-isocyano-4(2-isocyanopropyl)cyclohexane, 2,4-diisocyanopentane, 2-alkyl-1,3-diisocyanopropane, 1-isocyanobenzylisocyanamide, 1,2-diisocyanobenzene, 1,4-diisocyanocyclohexane, 1,8-diisocyanonaphthalene, 1,8-diisocyanofluorene, m-isocyanophenyl sulfone, 1,3-diisocyano-2,2,4,4-tetramethylcyclobutane, 1,3-diisocyano-2-hydroxy propane, 3,5-diisocyanobutane sulfonic acid or α,α'-diisocyano-o-xylene.

11. A reagent according to claim 10 in which the metal is rhodium and the biisocyanide is 1,3-diisocyanopropane and the Rhodium-rhodium separation is 3.26 Å.

12. A reagent according to claim 2 in which the secondary oxidant is selected from the group consisting of cerium salts, molybdenum salts, iron$^{+3}$, copper$^{+2}$, quinones, permanganates, $(IrCl_6)^{-2}$ or dichromates.

13. A reagent according to claim 13 further including a source of protons.

14. A method of oxidizing a substrate comprising the steps of:
  adding the substrate to a solution containing a dimeric, dinuclear transition metal complex containing four binucleating diisocyanide bridge ligands and a secondary oxidant which is a stronger oxidizing agent than the complex;
  bubbling oxygen through the solution; and
  recovering oxidized substrate from the solution.

15. A method according to claim 14 in which the oxygen is bubbled through as air.

16. A method according to claim 15 in which the substrate is a gas and is bubbled through the solution.

17. A method according to claim 16 in which the solution is at a temperature from 0° C. to 150° C. and is maintained at a pressure from 1 to 20 atmospheres.

18. A method according to claim 17 in which the concentration of the complex is from 10 to 200 ppm and the secondary oxidant is present is stoichiometric excess based on metal content of the complex.

19. A method according to claim 18 in which the transition metal is selected from the platinum group and the binucleating biisocyanide contains 2 to 20 carbon atoms and the substrate is an olefin.

* * * * *